(12) United States Patent
Buchanan et al.

(10) Patent No.: US 6,620,959 B1
(45) Date of Patent: Sep. 16, 2003

(54) PROCESS FOR THE PRODUCTION OF UNSYMMETRIC AND/OR SYMMETRIC DIALKYL CARBONATES AND DIOLS

(75) Inventors: J. Scott Buchanan, Lambertville, NJ (US); Zhaozhong Jiang, Edison, NJ (US); Jose Guadalupe Santiesteban, Bethlehem, PA (US); William A. Weber, Burlington, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/123,717

(22) Filed: Apr. 16, 2002

(51) Int. Cl.$^7$ .............................................. C07C 69/96
(52) U.S. Cl. ...................................... 558/277
(58) Field of Search .......................... 558/277

(56) References Cited

U.S. PATENT DOCUMENTS

| | | |
|---|---|---|
| 3,642,858 A | 2/1972 | Frevel et al. |
| 4,062,884 A | 12/1977 | Romano et al. |
| 4,181,676 A | 1/1980 | Buysch et al. |
| 4,218,391 A | 8/1980 | Romano et al. |
| 4,226,778 A | 10/1980 | Venturello et al. |
| 4,231,937 A | 11/1980 | Kao et al. |
| 4,233,221 A | 11/1980 | Raines et al. |
| 4,325,874 A | 4/1982 | Jacobson |
| 4,391,739 A | 7/1983 | Chu |
| 4,434,105 A | 2/1984 | Buysch et al. |
| 4,661,609 A | 4/1987 | Knifton |
| 4,686,274 A | 8/1987 | Harris et al. |
| 4,691,041 A | 9/1987 | Duranleau et al. |
| 4,895,970 A | 1/1990 | Harris |
| 5,015,753 A | 5/1991 | Harris |
| 5,218,135 A | 6/1993 | Buysch et al. |
| 5,231,212 A | 7/1993 | Buysch et al. |
| 5,292,980 A | 3/1994 | Dessau |
| 5,387,708 A | 2/1995 | Molzahn et al. |
| 5,391,803 A | 2/1995 | King et al. |
| 5,430,170 A | 7/1995 | Urano et al. |
| 5,436,362 A | 7/1995 | Kondoh et al. |
| 5,489,703 A | 2/1996 | Pacheco et al. |
| 5,498,743 A | 3/1996 | Shih et al. |
| 5,663,480 A | 9/1997 | Tsuneki et al. |
| 5,847,189 A | 12/1998 | Tojo et al. |
| 6,166,240 A | 12/2000 | Chang et al. |

FOREIGN PATENT DOCUMENTS

| | | |
|---|---|---|
| EP | 478 073 A2 | 1/1992 |
| JP | 54003012 | 1/1979 |
| JP | 3-44354 | 2/1991 |
| JP | 6-107601 | 4/1994 |

OTHER PUBLICATIONS

Watanabe, Yoshiaki et al., *Hydrotalcite–type Materials as Catalysts for the Synthesis of Dimethyl Carbonate from Ethylene Carbonate and Methanol*[1], Microporous and Mesoporous Materials, vol. 22, pp. 399–407, (1998).

Chin, Yu–Ren, et al., *Dimethyl Carbonate from Methanol by Non–Phosgenation Processes*, Process Economics Program, PEP Review No. 87–1–4, (Jul. 1988).

Knifton, John F., et al., *Ethylene Glycol–Dimethyl Carbonate Cogeneration*, Journal of Molecular Catalysis, vol. 67, pp. 389–399, (1991).

Chang, C.D., Handbook of Heterogenous Catalysis, *Methanol to Hydrocarbons*, Wiley–VCH: Weinheim, Germany, vol. 4, Chapter 3.7, pp. 1894–1908, (1997).

Cella, James A., et al., *Preparation of Dialkyl Carbonates via the Phase–Transfer–Catalyzed Alkylation of Alkali Metal Carbonate and Bicarbonate Salts*, J. Org. Chem., vol. 49, pp. 1122–1125 (1984).

Fujinami, Tatsuo et al., *A Facile Preparation of Dialkyl Carbonates from Potassium Carbonate and Alkyl Bromides by Using Organostannyl Compound as a Catalyst*, Chemistry Letters, pp. 749–752, (1981).

Romano, Ugo et al., *Synthesis of Dimethyl Carbonate from Methanol, Carbon Monoxide, adn Oxygen Catalyzed by Copper Compounds*, Ind. Eng. Chem. Prod. Res. Dev., vol. 19, pp. 396–403, (1980).

Tundo, Pietro et al., *Continuous–Flow Processes under Gas–Liquid Phase–Transfer Catalysis (GL–PTC) Conditions: The Reaction of Dialkyl Carbonates with Phenols, Alcohols, and Mercaptans*, Ind. Eng. Chem. Res., vol. 27, pp. 1565–1571, (1988).

Primary Examiner—Joseph K. McKane
Assistant Examiner—Ebenezer Sackey

(57) ABSTRACT

A process for the production of a dialkyl carbonate and a diol, such as dimethyl carbonate and ethylene glycol, by reacting a feed containing a cyclic carbonate, a hydroxy alkyl carbonate and an aliphatic monohydric alcohol in the presence of a transesterification catalyst is described. In another aspect, a process is described which is particularly useful for producing unsymmetric dialkyl carbonates, such as ethyl methyl carbonate.

23 Claims, 1 Drawing Sheet

PROCESS FOR THE PRODUCTION OF UNSYMMETRIC AND/OR SYMMETRIC DIALKYL CARBONATES AND DIOLS

This invention relates to a process for preparing unsymmetric and/or symmetric dialkyl carbonates and diols. More specifically the present invention relates to a process for preparing dialkyl carbonates and diols from the reaction product of cyclic carbonates, hydroxy alkyl carbonates and alcohols.

BACKGROUND OF THE INVENTION

Dialkyl carbonates are important intermediates for the synthesis of fine chemicals, pharmaceuticals and plastics and are useful as synthetic lubricants, solvents, plasticizers and monomers for organic glass and various polymers, including polycarbonate, a polymer known for its wide range of uses based upon its characteristics of transparency, shock resistance and processability.

One method for the production of polycarbonate resin employs phosgene and bisphenol-A as starting materials. However, this method has numerous drawbacks, including the production of corrosive by-products and safety concerns attributable to the use of the highly toxic phosgene. As such, polycarbonate manufacturers have developed non-phosgene methods for polycarbonate production, which use diphenyl carbonate and bisphenol-A as starting materials. Diphenyl carbonate can be prepared from phenol and dimethyl carbonate.

Dimethyl carbonate has a low toxicity and can also be used to replace toxic intermediates, such as phosgene and dimethyl sulphate, in many reactions, such as the preparation of urethanes and isocyanates, the quaternization of amines and the methylation of phenol or naphthols. Moreover, it is not corrosive and it will not produce environmentally damaging by-products. Dimethyl carbonate is also a valuable commercial product finding utility as an organic solvent, an additive for fuels, and in the production of other alkyl and aryl carbonates.

Dimethyl carbonate, as well as other dialkyl carbonates, have traditionally been produced by reacting alcohols with phosgene. These methods have the same problems as methods that use phosgene and bisphenol-A, i.e., the problems of handling phosgene and disposing of phosgene waste materials. Thus, there is a need for commercially viable non-phosgene methods for the production of dimethyl carbonate, as well as other dialkyl carbonates.

Non-phosgene methods that have been proposed for producing dialkyl carbonates include the transesterification reaction of alcohols and cyclic carbonates. Most of the proposed methods relate to the use of various catalysts for that reaction. Examples of such proposed catalysts include alkali metals or basic compounds containing alkali metals; tertiary aliphatic amines; thallium compounds; tin alkoxides; alkoxides of zinc, aluminum and titanium; a mixture of a Lewis acid and a nitrogen-containing organic base; phosphine compounds; quaternary phosphonium salts; cyclic amidines; compounds of zirconium, titanium and tin; a quaternary ammonium group-containing strongly basic anion-exchange solid material; a solid catalyst selected from the group consisting of a tertiary amine- or quaternary ammonium group-containing ion-exchange resin, a strongly acidic or a weakly acidic ion-exchange resin, a mixture of an alkali metal with silica, a silicate of an alkaline earth metal and an ammonium ion-exchanged zeolite; and a homogeneous catalyst selected from the group consisting of tertiary phosphine, tertiary arsine, tertiary stibine, a divalent sulfur compound and a selenium compound.

The catalytic transesterification of a cyclic carbonate with an alcohol generally involves two equilibrium steps which typically generates a hydroxyalkyl carbonate as the reaction intermediate. For example, in the transesterification of ethylene carbonate (EC) with methanol (MeOH), the intermediate which is formed is 2-hydroxyethyl methyl carbonate (HEMC). This two equilibrium step reaction may be represented by the following:

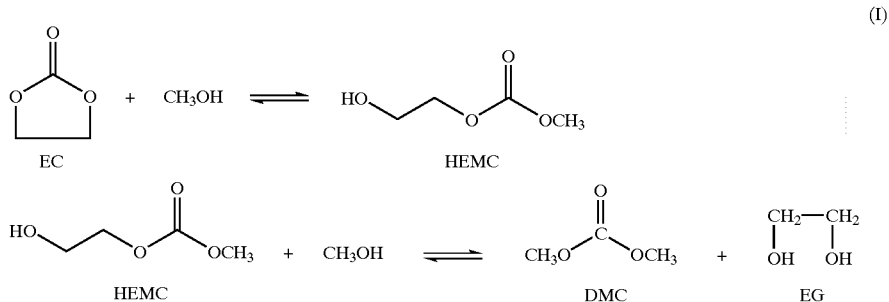

(I)

These reaction steps for converting the cyclic carbonate and alcohol to the dialkyl carbonate generally occur as two sequential steps. Addition of the first molecule of alcohol to the cyclic carbonate results in the production of the intermediate hydroxy alkyl carbonate. Addition of the second molecule of alcohol to the intermediate results in the production of the dialkyl carbonate and diol. The intermediate hydroxy alkyl carbonate generally builds to a maximum concentration faster than the equilibrium dialkyl carbonate concentration is reached. As a result of equilibrium constraints on the reactions, a maximum concentration (i.e., the equilibrium concentration) will be reached for the desired products. Thus, there is a limit to the yield for producing dialkyl carbonates and diols from cyclic carbonates and aliphatic monohydric alcohols for a given catalyst and reaction conditions.

Unsymmetric dialkyl carbonates, such as ethyl methyl carbonate (EMC), are useful as solvents for electrolytic solutions for lithium rechargeable batteries, solvents for resins and coating compositions, alkylating agents, or starting materials for carbamate synthesis.

Ethyl methyl carbonate, as well as other unsymmetric dialkyl carbonates, have traditionally been produced by esterification of alkyl chloroformate with alcohol under base (pyridine or amine) catalysis. Such methods have similar problems to the methods discussed above that use phosgene and bisphenol-A, i.e., highly reactive and highly toxic starting materials.

Other methods have been disclosed for the synthesis of unsymmetric dialkyl carbonates, which avoid the use of such highly toxic starting materials. One method involves an ester exchange reaction of a symmetric dialkyl carbonate with an alcohol having a different alkyl group under base catalysis. However, such a reaction typically results in a product, which includes a mixture of three dialkyl carbonates and two alcohols. For example, when a 1:1 molar ratio of DMC and EtOH is used as the starting materials, the product mixture will typically contain about a 45:45:10 molar ratio of DMC:EMC:DEC (diethyl carbonate) and a relative ratio of MeOH to EtOH of about 2:1. The mixture of these three dialkyl carbonates can result in difficult or costly purification steps to isolate the unsymmetric dialkyl carbonate, e.g., EMC.

Other methods which have been proposed include the disproportionation of two symmetrical dialkyl carbonates using a basic catalyst, e.g., an alkali metal alcoholate. However, such methods typically result in a product mixture of three dialkyl carbonates, including one unsymmetrical dialkyl carbonate. Again, this can result in difficult or costly purification steps to isolate the unsymmetric dialkyl carbonate from the three component mixture.

Thus, there is a need for a process for the production of symmetric and/or unsymmetric dialkyl carbonates and diols from starting materials which include cyclic carbonates and alcohols which does not have the above-mentioned disadvantages.

SUMMARY OF THE INVENTION

According to the present invention, it has now been found that unsymmetric and/or symmetric dialkyl carbonates and diols, and more specifically dimethyl carbonate and ethylene glycol, can be prepared with higher yields, from a feed containing a cyclic carbonate, a hydroxy alkyl carbonate and an aliphatic monohydric alcohol, compared to a feed containing only a cyclic carbonate and an aliphatic monohydric alcohol. In another aspect, it has been found that unsymmetric dialkyl carbonates can be produced, along with symmetric dialkyl carbonates, by selection of the hydroxy alkyl carbonate(s) present in the feed such that the hydroxy alkyl carbonate has an alkyl group which is different from the alkyl group in the aliphatic monohydric alcohol reactant.

The process of the present invention involves reacting a cyclic carbonate and a hydroxy alkyl carbonate with an aliphatic monohydric alcohol in the presence of a transesterification catalyst in a transesterification reaction zone to provide a dialkyl carbonate and a diol.

Preferably, the cyclic carbonate of the present invention is of the formula:

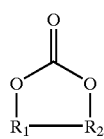
(II)

the hydroxy alkyl carbonate is of the formula:

(III)

the aliphatic monohydric alcohol is of the formula:

$$R_4-OH \qquad (IV)$$

wherein $R_1$ and $R_2$ independently of one another denote a divalent group represented by the formula $-(CH_2)_m-$, wherein m is an integer from 1 to 3, which is unsubstituted or substituted with at least one substituent selected from the group consisting of a $C_1-C_{10}$ alkyl group and a $C_6-C_{10}$ aryl group, wherein $R_1$ and $R_2$ can share the same substituent; and $R_3$ and $R_4$ independently of one another denote a monovalent aliphatic $C_1-C_{12}$ hydrocarbon group which is unsubstituted or substituted with at least one substituent selected from the group consisting of a $C_1-C_{10}$ alkyl group, a $C_2-C_{10}$ vinyl group or a $C_6-C_{10}$ aryl group.

In a preferred embodiment, the cyclic carbonate is ethylene carbonate, the hydroxy alkyl carbonate is 2-hydroxyethyl methyl carbonate, the aliphatic monohydric alcohol is methanol, the dialkyl carbonate is dimethyl carbonate and the diol is ethylene glycol.

The present invention provides the advantage of producing the desired dialkyl carbonates and diols in higher yield than that of a process which reacts only the cyclic carbonate and aliphatic monohydric alcohol. Also, the use of hydroxy alkyl carbonates having different alkyl groups than the alcohol provides unique mechanisms for producing unsymmetric dialkyl carbonates. The source of the hydroxy alkyl carbonate can be from a recycle stream of the present process or from any other source, including the product from other processes.

An integrated process for the production of a dialkyl carbonate and a diol from an alkylene oxide, carbon dioxide and an aliphatic monohydric alcohol comprising: (a) reacting an alkylene oxide with carbon dioxide in the presence of a carbonation catalyst at a temperature in the range of about 50° C. to 250° C. and at a pressure of at least about 1379 kPa (200 psi) to provide a crude cyclic carbonate stream comprising a cyclic carbonate and carbonation catalyst; and (b) reacting the cyclic carbonate and a hydroxy alkyl carbonate with the aliphatic monohydric alcohol in the presence of a transesterification catalyst, thereby producing a crude product stream comprising the dialkyl carbonate, the diol and the hydroxy alkyl carbonate; and (c) separating the hydroxy alkyl carbonate from the crude product stream and recycling the hydroxy alkyl carbonate to step (b).

Additional objects, advantages and novel features of the invention will be set forth in part in the description and examples which follow, and in part will become apparent to those skilled in the art upon examination of the following, or by practice of the invention. The objects and advantages of the invention may be realized and attained by means of the instrumentalities and combinations particularly pointed out in the appended claims.

DETAILED DESCRIPTION OF PREFERRED EMBODIMENTS

Figure 1:
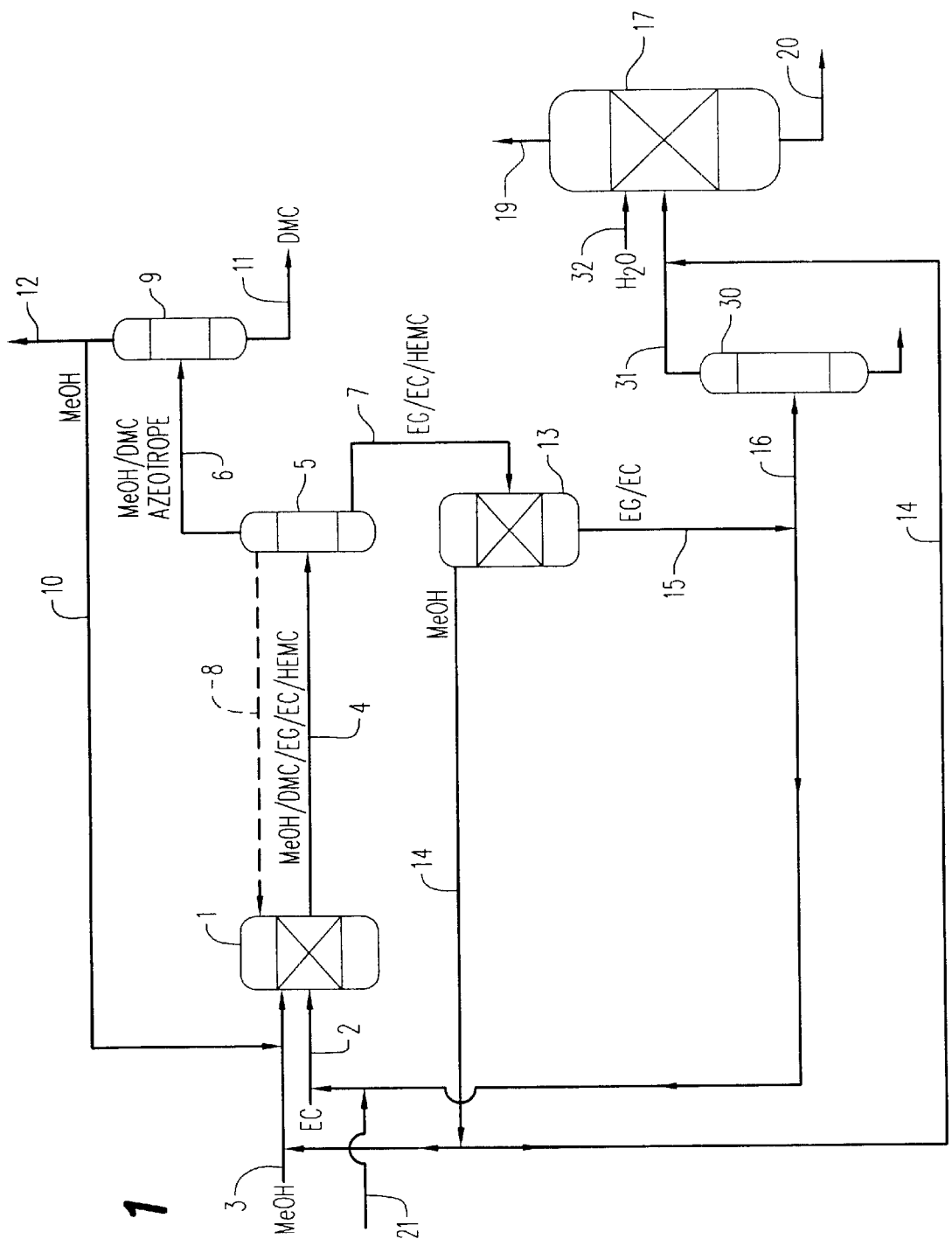
FIG. 1 is a schematic of an embodiment of the process which utilizes a heterogeneous transesterification catalyst.

A process for the production of dialkyl carbonates and diols from cyclic carbonates, hydroxy alkyl carbonates and aliphatic monohydric alcohols comprising reacting the cyclic carbonate and the hydroxy alkyl carbonate with the aliphatic monohydric alcohol in the presence of a transesterification catalyst.

Preferably the cyclic carbonate is of the formula:

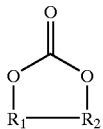
(II)

the hydroxy alkyl carbonate is of the formula:

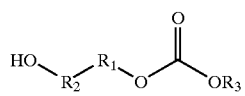
(III)

the aliphatic monohydric alcohol is of the formula:

wherein $R_1$ and $R_2$ independently of one another denote a divalent group represented by the formula —$(CH_2)_m$—, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent; and $R_3$ and $R_4$ independently of one another denote a monovalent aliphatic $C_1$–$C_{12}$ hydrocarbon group which is unsubstituted or substituted with at least one substituent selected from the group consisting of a $C_1$–$C_{10}$ alkyl group, a $C_2$–$C_{10}$ vinyl group or a $C_6$–$C_{10}$ aryl group.

In accordance with one embodiment according to the present invention, the cyclic carbonate is ethylene carbonate, the hydroxy alkyl carbonate is 2-hydroxy ethyl methyl carbonate, the aliphatic monohydric alcohol is methanol, the dialkyl carbonate is dimethyl carbonate and the diol is ethylene glycol. The dialkyl carbonate preferably comprises an unsymmetric dialkyl carbonate.

In accordance with still yet another embodiment, the cyclic carbonate is ethylene carbonate, the hydroxy alkyl carbonate is 2-hydroxy ethyl ethyl carbonate, the aliphatic monohydric alcohol is methanol, the dialkyl carbonate is ethyl methyl carbonate and the diol is ethylene glycol.

In accordance with another embodiment, the cyclic carbonate is ethylene carbonate, the hydroxy alkyl carbonate is a mixture of 2-hydroxy ethyl methyl carbonate and 2-hydroxy ethyl ethyl carbonate, the aliphatic monohydric alcohol is methanol, the dialkyl carbonate is a mixture of dimethyl carbonate and ethyl methyl carbonate and the diol is ethylene glycol.

The transesterification catalyst is at least one catalyst selected from the group consisting of a heterogeneous catalyst and a homogeneous catalyst. It is preferable that the reaction is carried out in the presence of a heterogeneous transesterification catalyst and in a fixed-bed flow reactor.

In preparing the dialkyl carbonates and diols, a cyclic carbonate and a hydroxy alkyl carbonate are reacted with an aliphatic monohydric alcohol in the presence of a transesterification catalyst. Preferably, the cyclic carbonate is represented by structural formula (II) above. Examples of such cyclic carbonates include ethylene carbonate, propylene carbonate, cyclohexene carbonate, cyclopentene carbonate, phenylethylene carbonate, and the like. Of these cyclic carbonates, ethylene carbonate and propylene carbonate are preferably used because of their good availability and high demand end products. Ethylene carbonate is most preferably used.

Preferably, the hydroxy alkyl carbonate is represented by structural formula (III) above. The particular hydroxy alkyl carbonate or mixtures of hydroxy alkyl carbonates which can be used will vary depending upon the particular cyclic carbonate present and the desired organic carbonate(s) and diol(s). Examples of such hydroxy alkyl carbonates include 2-hydroxy ethyl methyl carbonate, 2-hydroxy ethyl ethyl carbonate, 2-hydroxy ethyl 2-hydroxy cyclohexyl carbonate, 2-hydroxy ethyl 2-hydroxy cyclopentyl carbonate, 1-phenyl-1,2-ethanediol, and the like.

Of these hydroxy alkyl carbonates, 2-hydroxy ethyl methyl carbonate and 2-hydroxy ethyl ethyl carbonate are preferably used because of the high demand end products produced thereby. 2-hydroxy ethyl methyl carbonate is preferably used.

Preferably, the aliphatic monohydric alcohol is represented by structural formula (IV) above and has a boiling point lower than that of the produced diol. The type of aliphatic monohydric alcohol which can be used in the present invention varies depending on the particular cyclic carbonate and hydroxy alkyl carbonate present in the reaction mixture. Examples of such aliphatic monohydric alcohols include methanol, ethanol, n-propanol, iso-propanol, allyl alcohol, butanol (including isomers of butanol), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and the like. The above-mentioned aliphatic monohydric alcohol may be substituted with at least one substituent, such as a halogen atom, a $C_1$ to $C_{10}$ alkoxy group, a cyano group, an alkoxycarbonyl group, an aryloxycarbonyl group, an acyloxy group, a nitro group or the like.

Of these aliphatic monohydric alcohols, an alcohol having 1 to 6 carbon atoms is preferably used. When ethylene carbonate is the cyclic carbonate, an alcohol having 1 to 4 carbon atoms, i.e., methanol, ethanol, propanol (isomers) or butanol (isomers) is preferably used. The method of the present invention can be employed advantageously especially when methanol, ethylene carbonate and 2-hydroxy ethyl methyl carbonate are used as feedstocks for the transesterification reaction.

The transesterification reaction between the cyclic carbonate, the hydroxy alkyl carbonate and the aliphatic monohydric alcohol involves equilibrium steps which includes the formation of a hydroxy alkyl carbonate from the reaction of the cyclic carbonate with the aliphatic monohydric alcohol (Equation Va). The second step can involve two separate reaction pathways (Equations Vb and Vc), depending upon the particular cyclic carbonate, hydroxy alkyl carbonate and aliphatic monohydric alcohol present in the reaction mixture. The multiple equilibrium step reaction may be represented by the following:

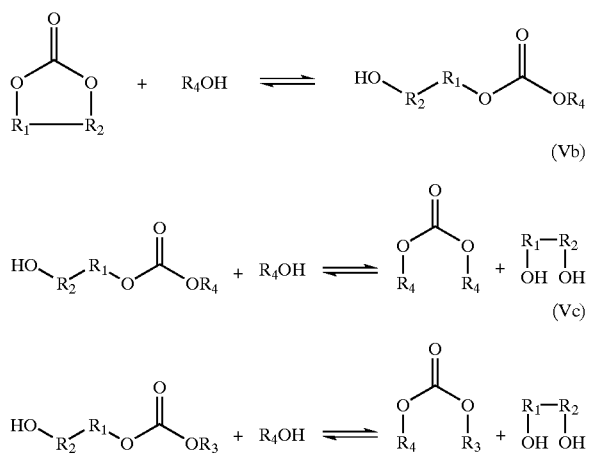

wherein $R_1$ and $R_2$ independently of one another denote a divalent group represented by the formula $-(CH_2)_m-$, wherein m is an integer from 1 to 3, which is unsubstituted or substituted with at least one substituent selected from the group consisting of a $C_1$–$C_{10}$ alkyl group and a $C_6$–$C_{10}$ aryl group, wherein $R_1$ and $R_2$ can share the same substituent; and $R_3$ and $R_4$ independently of one another denote a monovalent aliphatic $C_1$–$C_{12}$ hydrocarbon group which is unsubstituted or substituted with at least one substituent selected from the group consisting of a $C_1$–$C_{10}$ alkyl group, a $C_2$–$C_{10}$ vinyl group or a $C_6$–$C_{10}$ aryl group.

If it is desired to increase the yield of a desired symmetric dialkyl carbonate, groups $R_3$ and $R_4$ will be the same, and the second step reaction pathway will proceed according to Equation Vb. If, however, it is desired to produce an unsymmetric dialkyl carbonate, $R_3$ and $R_4$ will be different, resulting in a mixture of symmetric and unsymmetric dialkyl carbonates. The feed can contain two or more hydroxy alkyl carbonates, in which one hydroxy alkyl carbonate contains an $R_3$ group that is the same as the $R_4$ group and another hydroxy alkyl carbonate contains an $R_3$ group that is different from the $R_4$ group. The ratio of the different hydroxy alkyl carbonates can be selected to increase the yield of a particular dialkyl carbonate. Generally, in such a case, by increasing the amount of the hydroxy alkyl carbonate, containing an $R_3$ group which is different than the $R_4$ group, the amount of the unsymmetric dialkyl carbonate produced will increase.

The reactants to the transesterification reaction (i.e., the cyclic carbonate, the hydroxy alkyl carbonate and the aliphatic monohydric alcohol) are contacted in the presence of a transesterification catalyst. The transesterification catalyst can typically include any homogeneous or heterogeneous catalyst known in the art which provides adequate reaction kinetics and minimizes side reactions.

Examples of such catalysts include alkali metals or alkaline earth metals, such as lithium, sodium, potassium, rubidium, cesium, magnesium, calcium, strontium, barium and the like; basic compounds such as hydrides, hydroxides, alkoxides, aryloxides and amides of alkali metals or alkaline earth metals and the like; basic compounds, such as carbonates and hydrogencarbonates of alkali metals or alkaline earth metal, alkali metal or alkaline earth metal salts of organic acids and the like; tertiary amines such as triethylamine, tributylamine, trihexylamine, benzyldiethylamine and the like; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine, alkyltriazine and the like; cyclic amidines, such as diazabicycloundecene (DBU), diazabicyclononene (DBN) and the like; thallium compounds, such as thallium oxide, thallium halides, thallium hydroxide, thallium carbonate, thallium nitrate, thallium sulfate, thallium salts of organic acids and the like; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate and the like; zinc compounds, such as dimethoxyzinc, diethoxyzinc, ethylenedioxyzinc, dibutoxyzinc and the like; aluminum compounds such as aluminum trimethoxide, aluminum triisopropoxide, aluminum tributoxide and the like; titanium compounds, such as tetramethoxytitanium, tetraethoxytitanium, tetrabutoxytitanium, dichlorodimethoxytitanium, tetraisopropoxytitanium, titanium acetate, titanium acetylacetonate and the like; phosphorus compounds, such as trimethylphosphine, triethylphosphine, tributylphosphine, triphenylphosphine, tributylmethylphosphonium halides, trioctylbutylphosphonium halides, triphenylmethylphosphonium halides and the like; zirconium compounds, such as zirconium halides, zirconocenes, zirconium acetylacetonate, zirconium alkoxides, zirconium acetate and the like; lead and lead-containing compounds, e.g., lead oxides, such as $PbO$, $PbO_2$, $Pb_3O_4$ and the like; lead sulfides, such as $PbS$, $Pb_2S_3$, $PbS_2$ and the like; lead hydroxides, such as $Pb(OH)_2$, $Pb_3O_2(OH)_2$, $Pb_2[PbO_2(OH)_2]$, $Pb_2O(OH)_2$ and the like; plumbites, such as $Na_2PbO_2$, $K_2PbO_2$, $NaHPbO_2$, $KHPbO_2$ and the like; plumbates, such as $Na_2PbO_3$, $Na_2H_2PbO_4$, $K_2PbO_3$, $K_2[Pb(OH)_6]$, $K_4PbO_4$, $Ca_2PbO_4$, $CaPbO_3$, and the like; lead carbonates and basic salts thereof, such as $PbCO_3$, $PbCO_3 \cdot Pb(OH)_2$ and the like; alkoxylead compounds and aryloxylead compounds, such as $Pb(OCH_3)_2$, $(CH_3O)Pb(OPh)$, $Pb(OPh)_2$ and the like; lead salts of organic acids, and carbonates and basic salts thereof, such as $Pb(OCOCH_3)_2$, $Pb(OCOCH_3)_4$, $Pb(OCOCH_3)_2 \cdot PbO \cdot 3H_2O$, and the like; organolead compounds, such as $Bu_4Pb$, $Ph4Pb$, $Bu_3PbCl$, $Ph_3PbBr$, $Ph_3Pb$ (or $Ph_6Pb_2$), $Bu_3PbOH$, $Ph_2PbO$ and the like wherein Bu represents a butyl group and Ph represents a phenyl group; lead alloys, such as Pb—Na, Pb—Ca, Pb—Ba, Pb—Sn, Pb—Sb and the like; lead minerals, such as galena, zinc blend and the like; hydrates of these lead compounds; ion-exchangers, such as anion-exchange resins having tertiary amino groups, amide groups, or at least one type of ion-exchange group selected from the group consisting of sulfonate, carboxylate and phosphate groups; strongly basic solid anion-exchangers having quaternary ammonium groups as ion-exchange groups and the like; solid inorganic compounds, such as silica, silica-alumina, silica-magnesia, aluminosilicate, gallium silicate, various types of zeolites, various types of metal-exchanged zeolites, ammonium-exchanged zeolites; and the like.

Preferred homogeneous transesterification catalysts include alcoholates and alkali hydroxides and carbonates, such as sodium methylate and sodium hydroxide. Preferred heterogeneous transesterification catalysts include anion exchange resins having tertiary amine, quaternary ammonium, sulfonic acid or carboxylic acid functional groups, solid support catalysts containing alkaline earth metal halides, such as those described in U.S. Pat. No. 5,498,743, which is incorporated herein by reference, or inorganic solid support catalysts alone, such as alumina, pseudoboehmite, MgO and MgO/Al$_2$O$_3$ hydrotalcites, or containing ions, metals, compound or complexes of at least one element of Groups 1, 2, 4–10, 12 and 13–17 (IUPAC classification, previously Groups 1A, 2A, 4B–8B, 2B and 3A–7A) of the Periodic Table.

The specific catalyst is chosen to optimize the economics of the overall process and will depend upon the particular cyclic carbonate, hydroxy alkyl carbonate and aliphatic monohydric alcohol reacted, the type and amount of impurities contained in the feed and the transesterification reaction conditions. For example, it is contemplated that sodium hydroxide and quaternary ammonium anion exchange resins, containing some carbonate or bicarbonate anions, are particularly effective as transesterification catalysts for the synthesis of dimethyl carbonate and ethylene glycol in accordance with the present invention. The weight ratio of homogeneous catalyst to cyclic carbonate equivalents (cyclic carbonate+hydroxy alkyl carbonate) is typically about 0.0005:1 to 0.05:1, preferably about 0.002:1 to 0.01:1. In the case of a heterogeneous catalyst, the weight hourly space velocity (WHSV) will typically be from about 0.1 to about 30, preferably about 0.5 to about 15.

The transesterification reaction is preferably carried out in a continuous mode utilizing various reactor configurations, such as stirred-tank, tubular, fixed or packed-bed reactors, in a single or multiple-reactor configuration, a boiling pot surmounted by a trayed or packed column, or a reactive distillation column, at from about 50° C. up to about 250° C., preferably between about 75° C. up to about 140° C., and at pressures ranging from about atmospheric pressure up to about 14000 Kpa (2000 psi), preferably from about 140 Kpa (20 psi) up to about 2000 Kpa (300 psi). In the preferred mode of operation, the type of reactor, temperature and pressure are selected to insure a relatively high conversion and selectivity to the desired dialkyl carbonate and diol and to optimize the economics of the overall process. Generally, a reactive distillation column will tend to give higher conversions of ethylene carbonate and methanol, while a packed-bed reactor offers flexibility in handling various heterogeneous catalysts.

According to the present invention, it has now been found that overall yields for the dialkyl carbonate and diol can be improved if the hydroxy alkyl carbonate content in the feed to the transesterification reaction is maintained so that there is a weight ratio of hydroxy alkyl carbonate:cyclic carbonate of less than about 1000, preferably in the range from between about 0.01 to 100, and more preferably between about 0.1 to 10. The source of the hydroxy alkyl carbonate can be from a recycle stream of the present process or from any other source, including the product from other processes.

The effluent from the transesterification reaction will typically contain the dialkyl carbonate, diol, hydroxy alkyl carbonate, unreacted cyclic carbonate and unreacted aliphatic monohydric alcohol. Preferably, the hydroxy alkyl carbonate is recovered and recycled to the transesterification reaction in order to improve the product yields and improve overall process efficiency.

The transesterification reactor effluent stream will typically be fed to a series of separating apparatus to recover and recycle unreacted feed components and to recover the dialkyl carbonate and diol products. Examples of such separating apparatuses include a distillation type separating apparatus, an extractive distillation type separating apparatus, a liquid-liquid extraction type separating apparatus, a crystallization type separating apparatus, an absorption type separating apparatus and a membrane type separating apparatus. A combination of a plurality of different or identical separating apparatuses may be used. Among these separating apparatuses, a distillation type separating apparatus is especially preferred. The separated streams resulting from the use of the various separating apparatuses may also be subjected to further processing, such as additional reactions or incorporation into other chemical synthesis processes, as discussed more fully below.

One embodiment of the process, which utilizes a heterogeneous transesterification catalyst, is shown schematically in FIG. 1. Equipment not essential to the understanding of the invention such as heat exchangers, pumps, compressors and the like are not shown.

Referring now to FIG. 1, the transesterification reactor 1 is preferably a fixed bed reactor in which the cyclic carbonate and hydroxy alkyl carbonate are reacted with the aliphatic monohydric alcohol to form a dialkyl carbonate and a diol. The reactor, which contains the heterogeneous transesterification catalyst, is fed with cyclic carbonate and hydroxy alkyl carbonate via line 2 and with aliphatic monohydric alcohol via line 3. The molar ratio of alcohol to cyclic carbonate equivalents (cyclic carbonate+hydroxyl alkyl carbonate) fed to the reactor is generally from about 2:1 to about 6:1, preferably about 3:1 to about 4:1. The ratio of hydroxy alkyl carbonate:cyclic carbonate in the feed is generally less than about 1000, preferably in the range between about 0.01 to 100, and more preferably between about 0.1 to 10. In the case of dimethyl carbonate and ethylene glycol, the reaction of ethylene carbonate, 2-hydroxy ethyl methyl carbonate and methanol will be maintained at a temperature of about 80 to 200° C., preferably about 100 to 150° C., and pressures about 700 Kpa (100 psi) to 2000 Kpa (300 psi). The conversion per pass of ethylene carbonate equivalents (moles of EC and moles HEMC) to dimethyl carbonate is about 30 to 70%, preferably about 40 to 65%. The WHSV is generally about 0.3 to 3 hr$^{-1}$.

The transesterification reactor effluent is withdrawn from reactor 1 via line 4. The transesterification reactor effluent 4 will typically contain dialkyl carbonate, a diol, hydroxy alkyl carbonate, unreacted cyclic carbonate, unreacted alcohol, and some by-products such as organic oxygenates and polyglycols. For example, in the case of a transesterification reaction between ethylene carbonate, 2-hydroxyl ethyl methyl carbonate and methanol to provide dimethyl carbonate and ethylene glycol, major by-products can include dimethyl ether, 2-methoxyethanol and di-and tri-(ethylene) glycols, with the reactor effluent typically containing about 10 to 25 wt % dimethyl carbonate, about 7 to 23 wt % ethylene glycol, about 1 to 10 wt % 2-hydroxyethyl methyl carbonate, 10 to 35 wt % unreacted ethylene carbonate, about 30 to 50 wt % unreacted methanol, about 0.005 to 0.05 wt % dimethyl ether/2-methoxyethanol and about 0.01 to 0.1 wt % di- and tri-(ethylene) glycol. The composition, and byproduct yields in particular, can vary widely based upon the specific catalysts and operating conditions employed.

The transesterification reactor effluent is fed from line 4 into a distillation column 5, where an overhead product stream containing the dialkyl carbonate, alcohol and organic oxygenates is removed via line 6 and a bottoms product stream containing the diol, cyclic carbonate, hydroxy alkyl carbonate and polyglycols is removed via line 7. In the case of dimethyl carbonate and ethylene glycol, the distillation column is typically operated at a pressure of between about 5 and 30 psia and a temperature range at the top of the column 5 of about 50 to 90° C. Optionally, a side-draw stream 8, which is depleted of the diol and cyclic carbonate, is withdrawn from column 5 and recycled to transesterification reactor 1, to reduce the load on the dialkyl carbonate product distillation column 9.

The overhead product stream is fed via line 6 to a dialkyl carbonate product distillation column 9, where the alcohol is taken overhead and recycled via lines 10 and 3 to transesterification reactor 1 and dialkyl carbonate product is removed from the bottom via line 11 and sent to storage. A purge stream 12 is also provided to prevent the accumulation of light byproduct impurities. In the case of dimethyl carbonate, the dialkyl carbonate product distillation column 9 is typically operated at a pressure of about 120 psia to 200 psia and a temperature range of about 120 to 190° C. Dimethyl carbonate and methanol form a low-boiling azeotrope, so that the overhead stream 10 can include up to about 15 wt %, more typically about 5–15 wt % dimethyl carbonate. This dimethyl carbonate is generally recycled to the transesterification reactor along with the methanol.

The bottoms product stream from distillation column 5 is fed via line 7 to a diol product distillation column 13, where the diol product is removed overhead via line 14 and sent to storage or further processing (as discussed below), and a bottoms stream containing cyclic carbonate, hydroxy alkyl carbonate, polyglycols and other heavies is removed via line 15. In the case of ethylene glycol, the distillation column is operated in a temperature range of about 100 to 170° C., under a vacuum in the range of about 200 to 50 mm Hg. It may be desirable to operate in the less severe range of conditions, and sacrifice some diol recovery, to avoid side reactions involving the hydroxy alkyl carbonate, depending upon the overall economics of the process. In such a case the bottoms stream may contain small amounts of the desired diol product. The bottoms stream 15 is recycled to the transesterification reactor via lines 15 and 2. A purge stream 16 is provided to prevent an accumulation of polyglycols and other heavies. Optionally, an evaporator 30 can be employed to recover additional cyclic carbonate, hydroxy alkyl carbonate and diol (if present) from the purge stream 16. In the case of ethylene carbonate and 2-hydroxy ethyl methyl carbonate, the operating conditions of the optional evaporator typically include temperatures in the range of about 120 to 180° C., under a vacuum in the range of about 10 to 80 mmHg.

In another embodiment, a hydrolysis reactor 17 can be incorporated into the process to provide a highly purified diol, e.g. ethylene glycol. The feed to this hydrolysis reactor includes the diol product stream 14, which typically contains small amounts of cyclic carbonate. Optionally, cyclic carbonate and diol (if present) recovered overhead from purge stream 16 can also be fed to the hydrolysis reactor 17 via conduit 31. Stoichiometric amount of water is fed via line 32 to hydrolysis reactor 17. $CO_2$ is removed from the hydrolysis reactor 17 overhead via line 19 and a bottoms product stream containing high purity diol is removed via line 20.

In yet another embodiment, which utilizes a homogeneous transesterification catalyst, reference will again be made to FIG. 1. In this embodiment the transesterification reactor effluent 4 will contain homogeneous transesterification catalyst, in addition to the other components mentioned above. The catalyst will remain with the bottoms product stream 7, following distillation in column 5. The bottoms product stream 7 can be fed to an evaporator to separate the catalyst from the bottoms product stream 7 and the separated catalyst can be recycled to the transesterification reactor 1. Optionally, the catalyst will remain in the bottoms product stream 7 until it is recycled with the cyclic carbonate and hydroxy alkyl carbonate in bottoms stream 15. Again, evaporator 30 can be employed to recover additional cyclic carbonate, hydroxy alkyl carbonate and homogeneous transesterification catalyst from purge stream 16. Make-up homogeneous transesterification catalyst is fed into line 21.

EXAMPLES

The following examples have been carried out to illustrate preferred embodiments of the invention. These examples include production of dimethyl carbonate (DMC) and ethylene glycol (EG) from feeds containing 2-hydroxy ethyl methyl carbonate (HEMC) at different temperatures and different levels of methanol (MeOH); comparative examples for the production of DMC and EG at similar temperatures and MeOH levels, but with no HEMC; and the production of both DMC and ethyl methyl carbonate (EMC) in the presence of MeOH.

Example 1

Dimethyl carbonate (DMC) and ethylene glycol (EG) were prepared in the presence of a MgO heterogeneous catalyst. The MgO catalyst was utilized in a fixed-bed catalytic experiment as follows: 2 grams of an industrial prepared MgO material was loaded into a ⅜" tubular stainless steel reactor. The physical properties and composition of the MgO material are summarized in Table 1 below.

TABLE 1

| Physical Properties of MgO catalyst | | | | | |
|---|---|---|---|---|---|
| Ash, wt % | Bet surface Area m²/g | Al, ppm | Fe, ppm | Na, ppm | Ca, wt % |
| 95.7 | 145 | 280 | 680 | 540 | 0.64 |

A feed was prepared, Feed 1, containing 54.9 wt % methanol (MeOH), 3.2 wt % ethylene glycol (EG), 10.9 wt % 2-hydroxyethyl methyl carbonate (HEMC), 30.7 wt % ethylene carbonate (EC) and 0.2 wt % other. The composition of Feed 1 is also shown below in Tables 2 and 3 in wt % and mole %, respectively.

Feed 1 was passed over the MgO catalyst at a pressure of 100 psig, a temperature of 200° F. and a LHSV of 1 hr$^{-1}$. The experiment was repeated, but at a temperature of 250° F.

The reactor effluent at each temperature was analyzed by GC. The results at each of the temperatures are shown in Table 4 below.

Example 2

A feed was prepared, Feed 2, containing 56.6 wt % MeOH, 3.3 wt % EG, 0.0 wt % HEMC, 39.9 wt % EC and 0.2 wt % other. The composition of Feed 2 is also shown below in Table 2 and 3 in wt % and mole %, respectively.

Example 1 was repeated, using Feed 2 instead of Feed 1. The results at each temperature for Feed 2 are shown in Table 4 below.

Example 3

A feed was prepared, Feed 3, containing 39.8 wt % MeOH, 4.3 wt % EG, 14.5 wt % HEMC, 41.0 wt % EC and 0.3 wt % other. The composition of Feed 3 is also shown below in Tables 2 and 3 in wt % and mole %, respectively.

Example 1 was repeated, using Feed 3 instead of Feed 1. The results at each temperature for Feed 3 are shown in Table 5 below.

Example 4

A feed was prepared, Feed 4, containing 41.4 wt % MeOH, 4.5 wt % EG, 0.0 wt % HEMC, 53.8 wt % EC and 0.3 wt % other. The composition of Feed 4 is also shown below in Tables 2 and 3 in wt % and mole %, respectively.

Example 1 was repeated using Feed 4 instead of Feed 1. The results at each temperature for Feed 4 are shown in Table 5 below.

TABLE 2

Feed Composition in weight %

| Component | Feed 1 | Feed 2 | Feed 3 | Feed 4 |
|---|---|---|---|---|
| Methanol (MeOH) | 54.9% | 56.6% | 39.8% | 41.4% |
| Ethylene glycol (EG) | 3.2% | 3.3% | 4.3% | 4.5% |
| 2-hydroxyethylmethylcarbonate (HEMC) | 10.9% | 0.0% | 14.5% | 0.0% |
| Ethylene carbonate (EC) | 30.7% | 39.9% | 41.0% | 53.8% |
| Other | 0.2% | 0.2% | 0.3% | 0.3% |

TABLE 3

Feed Composition in mole %

| Component | Feed 1 | Feed 2 | Feed 3 | Feed 4 |
|---|---|---|---|---|
| Methanol (MeOH) | 77.4% | 77.6% | 65.0% | 65.3% |
| Ethylene glycol (EG) | 2.4% | 2.4% | 3.7% | 3.7% |
| 2-hydroxyethylmethylcarbonate (HEMC) | 4.1% | 0.0% | 6.3% | 0.0% |
| Ethylene carbonate (EC) | 15.7% | 19.9% | 24.3% | 30.8% |
| Other | 0.5% | 0.1% | 0.7% | 0.2% |

A review of Table 3 reveals that Feeds 1 and 2, and Feeds 3 and 4, respectively, have approximately the same mole equivalents of MeOH and approximately the same EC mole equivalents. EC mole equivalents refers to the moles of EC+HEMC.

TABLE 4

Conversion of Feeds containing 2-Hydroxyethylmethlcarbonate and Ethylene Carbonate in the Presence of Methanol to DMC

| Feed Temperature, ° F. | Feed 1 200 | Feed 2 200 | Feed 1 250 | Feed 2 250 |
|---|---|---|---|---|
| Component (wt %) | | | | |
| Methanol | 48.1% | 46.4% | 42.0% | 42.7% |
| Dimethyl Carbonate | 11.0% | 11.9% | 21.3% | 18.0% |
| Ethylene glycol | 11.2% | 12.2% | 17.1% | 16.1% |
| 2-Hydroxylethylmethyl carbonate | 7.2% | 6.4% | 3.1% | 5.2% |
| Ethylene carbonate | 22.0% | 22.3% | 16.1% | 17.6% |
| Other | 0.6% | 0.6% | 0.5% | 0.5% |
| Conversion of EC Equivalents | 28.3% | 30.2% | 53.1% | 45.2% |
| DMC Yield (g of DMC/100 g of feed) | 11.00 | 11.95 | 21.26 | 17.98 |

TABLE 5

Conversion of Feeds containing 2-Hydroxyethylmethylcarbonate and Ethylene Carbonate in the Presence of Methanol to DMC

| Feed Temperature, ° F. | Feed 3 200 | Feed 4 200 | Feed 3 250 | Feed 4 250 |
|---|---|---|---|---|
| Component (wt %) | | | | |
| Methanol | 35.0% | 33.6% | 28.6% | 30.1% |
| Dimethyl Carbonate | 8.5% | 7.0% | 19.7% | 13.6% |
| Ethylene glycol | 10.0% | 9.9% | 16.7% | 14.2% |
| 2-Hydroxylethylmethy Carbonate | 8.7% | 10.6% | 4.9% | 5.8% |
| Ethylene carbonate | 37.0% | 38.2% | 29.4% | 35.8% |
| Other | 0.8% | 0.6% | 0.7% | 0.6% |
| Conversion of EC Equivalents | 16.0% | 13.0% | 36.9% | 25.0% |
| DMC Yield (g of DMC/100 g of feed) | 8.46 | 7.03 | 19.75 | 13.64 |

A review of Tables 4 and 5 reveals that the conversion of EC equivalents (moles of EC+moles of HEMC) to DMC is generally higher for feeds containing HEMC (Feeds 1 and 3) than for feeds containing no HEMC (Feeds 2 and 4). This is particularly apparent for higher temperature (i.e., 250° F.) and feeds containing the least MeOH (Feeds 3 and 4).

Example 5

A feed containing 2-hydroxy ethyl ethyl carbonate (HEEC) was prepared for use in a fixed bed catalytic experiment. The feed composition is shown below in Table 5.

TABLE 5

Composition of Feed containing 2-Hydroxyethylethyl Carbonate

| Component | Wt % |
|---|---|
| Methanol | 47.3% |
| Ethanol | 5.6% |
| 2-hydroxylethylmethycarbonate | 7.8% |
| Ethylene carbonate | 22.9% |
| 2-hydroxyethylethylcarbonate | 16.2% |
| Other | 0.2% |

This feed was passed over the MgO catalyst at 100 psig, a LHSV of 1 hr$^{-1}$ and at temperatures of 200° F. and 250° F., as in Example 1. The composition of the reactor effluent and results of the reaction for each temperature are shown below in Table 6.

TABLE 6

Conversion of Feeds containing 2-Hydroxyethylethyl Carbonate In the Presence of Methanol to Ethylmethyl Carbonate

| Temperature, ° F. | 200 | 250 |
|---|---|---|
| Component, wt % | | |
| Methanol | 42.1% | 37.3% |
| Ethanol | 9.7% | 9.7% |
| Dimethylcarbonate (DMC) | 6.8% | 15.2% |
| Ethylene glycol | 6.4% | 12.4% |
| Ethylmethylcarbonate (EMC) | 1.5% | 2.9% |
| 2-hydroxylethylmethylcarbonate | 14.5% | 9.3% |
| Ethylene carbonate | 16.8% | 11.9% |
| 2-hydroxyethylethylcarbonate | 2.1% | 1.2% |
| Conversion of 2-hydroxyethylethylcarbonate | 86.8% | 92.4% |
| Selectivity to | | |
| Ethanol + ethylene carbonate | 86.1% | 75.7% |
| Ethylmethylcarbonate (EMC) | 13.9% | 24.3% |

A review of Table 6 reveals that significant amounts of both DMC and ethyl methyl carbonate (EMC) were formed in the reaction. It appears that HEEC reacts with MeOH to form EMC and that for each mole of EMC formed, one mole of EG forms. Additionally, it appears that some of the HEEC decomposed to ethanol (EtOH) and EC. As such, the selectivities to each of the reaction pathways for the HEEC has been calculated.

We claim:

1. A process for the production of dialkyl carbonates and diols from cyclic carbonates, hydroxy alkyl carbonates and aliphatic monohydric alcohols comprising reacting said cyclic carbonate and said hydroxy alkyl carbonate with said aliphatic monohydric alcohol in the presence of a transesterification catalyst.

2. A process according to claim 1, wherein said cyclic carbonate is of the formula:

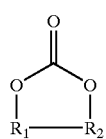
(II)

said hydroxy alkyl carbonate is of the formula:

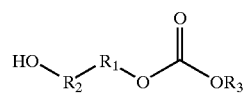
(III)

said aliphatic monohydric alcohol is if the formula:

wherein $R_1$ and $R_2$ independently of one another denote a divalent group represented by the formula —$(CH_2)_m$—, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent; and $R_3$ and $R_4$ independently of one another denote a monovalent aliphatic $C_1$–$C_{12}$ hydrocarbon group which is unsubstituted or substituted with at least one substituent selected from the group consisting of: a $C_1$–$C_{10}$ alkyl group, a $C_2$–$C_{10}$ vinyl group and a $C_6$–$C_{10}$ aryl.

3. A process according to claim 2, wherein said cyclic carbonate is ethylene carbonate, said hydroxy alkyl carbonate is 2-hydroxy ethyl methyl carbonate, said aliphatic monohydric alcohol is methanol, said dialkyl carbonate is dimethyl carbonate and said diol is ethylene glycol.

4. A process according to claim 2, wherein said dialkyl carbonate comprises an unsymmetric dialkyl carbonate.

5. A process according to claim 4, wherein said cyclic carbonate is ethylene carbonate, said hydroxy alkyl carbonate is 2-hydroxy ethyl ethyl carbonate, said aliphatic monohydric alcohol is methanol, said unsymmetric dialkyl carbonate is ethyl methyl carbonate and said diol is ethylene glycol.

6. A process according to claim 2, wherein said dialkyl carbonate comprises a mixture of an unsynmmetric dialkyl carbonate and a symmetric dialkyl carbonate.

7. A process according to claim 6, wherein said cyclic carbonate is ethylene carbonate, said hydroxy alkyl carbonate is a mixture of 2-hydroxy ethyl methyl carbonate and 2-hydroxy ethyl ethyl carbonate, said aliphatic monohydric alcohol is methanol, said dialkyl carbonate is a mixture of dimethyl carbonate and ethyl methyl carbonate and said diol is ethylene glycol.

8. A process according to claim 1, wherein said transesterification catalyst is at least one catalyst selected from the group consisting of a heterogeneous catalyst and a homogeneous catalyst.

9. A process according to claim 1, wherein the reaction is carried out in the presence of a heterogeneous transesterification catalyst and in a fixed bed flow reactor.

10. A process according to claim 9, wherein the reaction occurs at a temperature in the range of from about 20 to 300° C. and a pressure of from about 14 to 4000 psig.

11. A process according to claim 1, wherein the reaction occurs at a temperature of at least about 250° C.

12. The process according to claim 1, wherein the molar ratio of said hydroxy alkyl carbonate to said cyclic carbonate is in the range between about 0.01:1,000 to about 0.01:100.

13. The process according to claim 12, wherein said molar ratio of hydroxy alkyl carbonate to said cyclic carbonate is about 0.1:10.

14. The process according to claim 1, wherein said aliphatic monohydric alcohol and said hydroxy alkyl carbonate have different alkyl groups.

15. The process according to claim 1, wherein the molar ratio of said aliphatic monohydric alcohol to said cyclic carbonate equivalents is in the range between about 2:1 to about 6:1.

16. The process according to claim 15, wherein the molar ratio of said aliphatic monohydric alcohol to said cyclic carbonate equivalents is in the range between about 3:1 to about 4:1.

17. The process according to claim 3, wherein the reaction is conducted at a temperature between about 80 to 200° C. and a pressure between about 700 Kpa (100 psi) to about 2000 Kpa (300 psi).

18. The process according to claim 17, wherein the conversion of said ethylene carbonate to said dimethyl carbonate is between about 30 to about 70%.

19. The process according to claim 18, wherein the conversion of said ethylene carbonate to said dimethyl carbonate is between about 40 to 65%.

20. The process according to claim 1, wherein the reaction occurs at a temperature of between about 50 to about 250° C. and a pressure of between about atmospheric to about 14,000 Kpa (2000 psi).

21. The process according to claim 20, wherein the reaction occurs at a temperature of between about 75 to about 140° C. and a pressure of between about 140 Kpa (20 psi) to about 2,000 Kpa (300 psi).

22. A process according to claim 1, wherein $R_3$ and $R_4$ are the same and said dialkyl carbonate is symmetric.

23. A process according to claim 1, wherein $R_3$ and $R_4$ are different and said dialkyl carbonate is unsymmetric.

* * * * *